US00PP25876P2

(12) United States Plant Patent
Ault

(10) Patent No.: US PP25,876 P2
(45) Date of Patent: Sep. 8, 2015

(54) ***BAPTISIA* PLANT NAMED 'LAVENDER ROSE'**

(50) Latin Name: ***Baptisia* hybrid**
Varietal Denomination: Lavender Rose

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 67 days.

(21) Appl. No.: 13/999,436

(22) Filed: Feb. 25, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Penny J. Aguirre

(57) ABSTRACT

A new cultivar of *Baptisia*, 'Lavender Rose' that is characterized by its upright, vase-shaped plant habit at anthesis that becomes a broad, uniformly rounded mound as the growing season progresses, its densely clustered green stems that do not lodge, its racemes of flowers that are medium to dark violet-blue in color at anthesis aging to a violet-purple color depending on ambient temperatures, its large flowers that are an average of 2.5 cm in width, its dense foliage that completely masks the bases of the flowering stems at maximum foliage growth, and its vigorous growth rate.

2 Drawing Sheets

Botanical classification: *Baptisia* hybrid.
Cultivar designation: 'Lavender Rose'.

BACKGROUND OF THE INVENTION

The present invention relates to a new and distinct cultivar of hybrid *Baptisia* plant, botanically known as *Baptisia* 'Lavender Rose' and will be referred to hereafter by its cultivar name, 'Lavender Rose'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Lavender Rose' was selected as a single unique plant by the Inventor in June of 2009 after evaluating seedlings that derived from a cross made in May of 2004 between unnamed plants of hybrid *Baptisia* from the Inventor's breeding program. The female parent was a seedling that derived from open pollination of an unnamed interspecific hybrid of *Baptisia australis*×*Baptisia leucophaea*. The male parent was an unnamed interspecific hybrid of *Baptisia australis*×*Baptisia leucophaea*.

Asexual propagation of the new cultivar was first accomplished by stem tip cuttings under the direction of the Inventor in June of 2009 in Glencoe, Ill. Asexual propagation by stem shoot tip cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Lavender Rose' as a unique cultivar of *Baptisia*.

1. 'Lavender Rose' exhibits an upright, vase-shaped plant habit at anthesis that becomes a broad, uniformly rounded mound as the growing season progresses.
2. 'Lavender Rose' exhibits densely clustered green stems that do not lodge.
3. 'Lavender Rose' exhibits racemes of flowers that are medium to dark violet-blue in color at anthesis and aging to a violet-purple color, depending on ambient temperatures.
4. 'Lavender Rose' produces large flowers that are an average of 2.5 cm in width.
5. 'Lavender Rose' exhibits dense foliage that completely masks the bases of the flowering stems at maximum foliage growth.
6. 'Lavender Rose' exhibits a vigorous growth rate.

The female parent of 'Lavender Rose' differs from 'Lavender Rose' in having a spreading, irregular and more open plant habit, in having stems that lodge, and in having flowers that are medium blue-violet in color. The male parent differs from 'Lavender Rose' in having an irregular plant habit that is taller than it is wide, in being larger in size, and in having less dense stems that tend to lodge after summer rains.

'Lavender Rose' can be most closely compared to the *Baptisia* cultivars 'Royal Purple' (U.S. Plant patent application Ser. No. 13/987,050)* and 'Purple Smoke' (not patented). 'Royal Purple' is similar to 'Lavender Rose' in having flowers that are dark violet in color and in having a plant habit that grows wider than tall over time. 'Royal Purple' differs from 'Lavender Rose' in having a vase shaped habit with broadly rounded irregular shaped head of foliage with flowering stems bases that are visible below the foliage, in having fewer flowers per raceme, and in having flowers that are persistently dark violet in color. 'Purple Smoke' is similar to 'Lavender Rose' in having flowers that are violet in color, in having a three week long flowering season that begins in mid-May, and in having a bushy rounded plant habit. 'Purple Smoke' differs from 'Lavender Rose' in having stems that are gray in color, in being taller and narrower in size, in rarely, if ever, producing fruit with viable seed, and in having readily visible bases of the flowering stems beneath the foliage.

*Applicant gives Examiner permission to replace the U.S. Plant Patent Application No. with the U.S. Patent No. if applicable and delete this statement.

BRIEF DESCRIPTION OF THE DRAWINGS

The accompanying colored photographs illustrate the overall appearance and distinct characteristics of the new *Baptisia*. The photographs in FIGS. 1 and 2 were taken of a plant four years in age and the photograph in FIG. 3 was taken of a plant 9 years in age as grown outdoors in a trial plot in Glencoe, Ill.

The photograph in FIG. 1 provides a close-up view of an inflorescence of 'Lavender Rose'.

Figure 1:
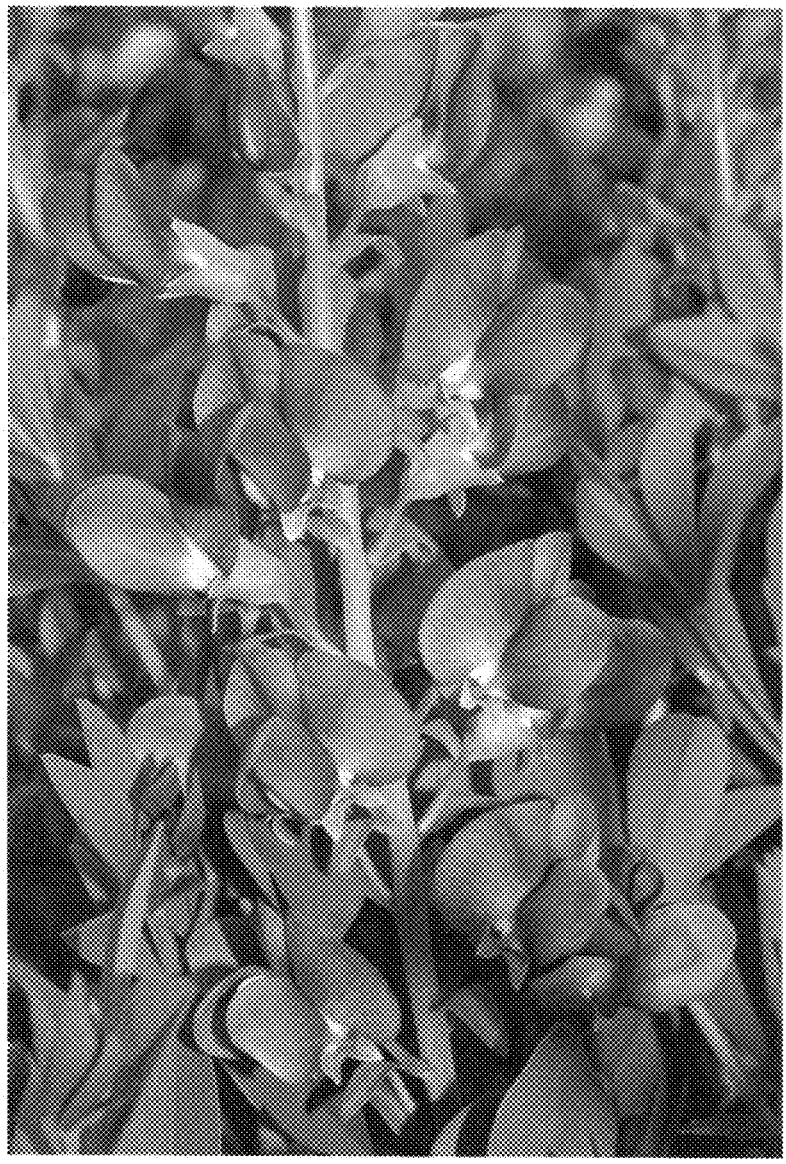
Figure 2:
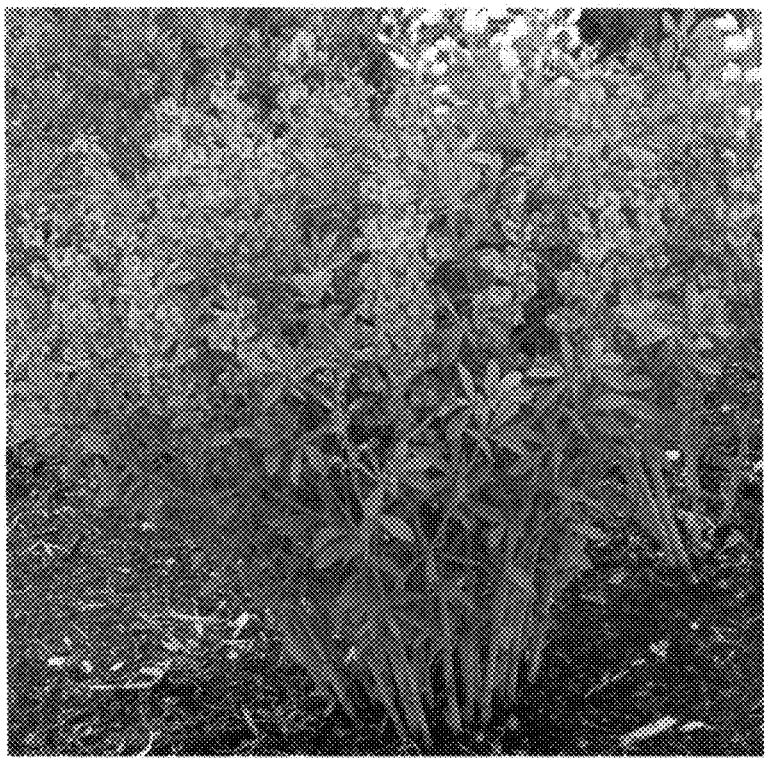

The photograph in FIG. 2 provides a side view of 'Lavender Rose' in bloom and illustrates the plant habit and flowering habit.

Figure 3:
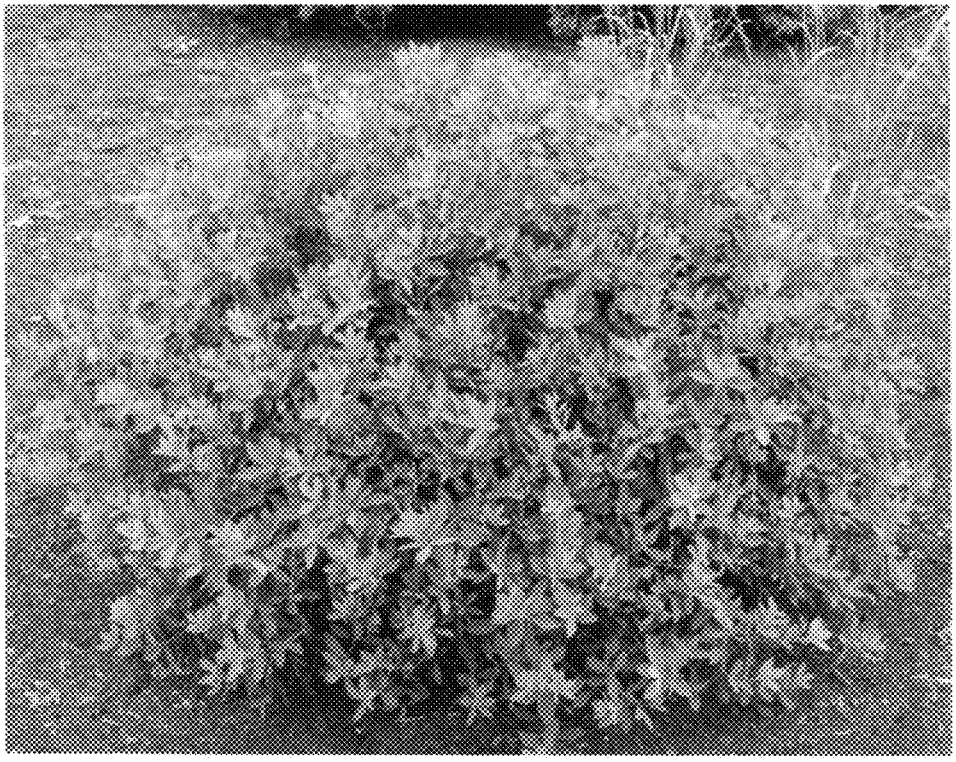

The photograph in FIG. 3 provides a side view of the late summer foliage of 'Lavender Rose'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of five year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of 3 weeks from mid to late May to early June in Glencoe, Ill.

*Plant habit*.—Upright, vase-shaped plant habit at anthesis that becomes a broad, uniformly rounded mound as the growing season progresses.

*Height and spread*.—Up to 1.5 m in width and 1 m in height.

*Hardiness*.—U.S.D.A. Zones 4 to 8.

*Diseases and pests*.—No susceptibility to diseases or pests has been observed.

*Root description*.—Fibrous and fine.

*Propagation*.—Rooting of stem tip cuttings.

*Growth rate*.—Vigorous.

Stem description:

*Branch habit*.—Densely branched; a five year old plant produced 21 stems, each with an average of 3 secondary branches and 2 tertiary branches per secondary branch.

*Stem size*.—Main stem; an average of 73 cm (including peduncle) in length and 6 mm in width (9 mm at base), secondary; average of 17 cm in length and 4 mm in width, tertiary; an average of 5.5 cm in length and 2 mm in width.

*Stem shape*.—Oval.

*Stem color*.—A blend of 137B and 137C.

*Stem surface*.—Glabrous, satiny but slightly glaucous.

Foliage description:

*Leaf shape*.—Fan-shaped in overall outline.

*Leaf division*.—3-palmate.

*Leaf internode*.—Foliage present close to base, an average of 6.5 cm on main stem and secondary branches.

*Leaf size*.—Average of 5 cm in length and 7 cm in width.

*Leaf quantity*.—Average of 22 per stem.

*Leaflet shape*.—Oblanceolate.

*Leaflet base*.—Cuneate.

*Leaflet apex*.—Acute.

*Leaflet venation*.—Pinnate pattern, not conspicuous, color matches leaflet color on the upper and lower surface with the basal portion of the mid ribs on lower surface 138B.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded and mature; upper and lower surface 137B.

*Leaflet size*.—Average of 4.5 cm in length and 1.4 cm in width.

*Petioles*.—Average of 4 mm in length and 1.5 mm in width, clasping to stem at mature nodes, 138B in color, surface is glabrous and satiny.

*Stipules*.—On basal 2 to 3 nodes prior to leaves; single, lanceolate in shape, up to 4.5 cm in length and 1.5 cm in width, truncate base, acuminate apex, 137A in color.

Flower description:

*Inflorescence type*.—Terminal racemes of pea-like flowers on main and secondary branches, blooms from the base to the apex.

*Inflorescence size*.—Average of 45 cm in length and 2.5 cm in width.

*Lastingness of inflorescence*.—An average of 3 weeks.

*Flower size*.—Average of 2.7 cm in depth and about 2.2 cm in diameter.

*Flower fragrance*.—Faint.

*Flower number per inflorescence*.—Average of 40.

*Peduncle*.—Oval in shape, up to 32 cm in length and an average of 3.5 mm in width, 138B in color, surface is glabrous, satiny and slightly glaucous, flower internode length averages from whorls to about 1.2 cm.

*Petiole*.—Average of 1.5 cm in length, about 1.5 mm in width, oval in shape, 138A in color, glabrous and satiny surface.

*Flower buds*.—Kidney-shaped, about 2.5 cm in length and 1 cm in width, color of petal portion is a blend of 90C and 91A and a sliver of exposed keel portion 145C, calyx portion same as open flowers.

*Flower type*.—Papilionaceous, held at about a 45° angle.

*Calyx*.—Campanulate, about 1.2 cm in length and 1.3 cm in diameter, surface is glabrous and satiny, 138B in color, persistent.

*Sepals*.—5, fused with the exception of apex of each, free portion is triangular in shape 6 mm in width and 5 mm in depth with an acute apex, 138B in color on outer and inner surface.

*Corolla features*.—Papilionaceous (4 segments) with a keel, a banner and 2 lateral wings, lateral wings; obelliptic in shape, about 2 cm in length and 1 cm in width, color on outer surface and the inner surface is a blend of 90C and 91A, and blending with N82A as the flower ages, basal portion 4D, rounded apex, oblique base, keel; only partially visible, comprised of 2 segments surrounding reproductive organs, oblong (slightly oblique) in shape with rounded apex and oblique base, 1.7 cm in length and 1 cm in width, upper surface and lower surface are 145C in color, banner; orbicular in shape, reflexed, about 2 cm in length and 2.5 cm in width, upper and lower surface is a blend of 90C and 91A, and blending with N82A as the flower ages, basal portion 145B and mid section marked with 4D, apex is rounded with a single notch, surface is glabrous on all sections.

*Receptacle*.—Disk-shaped, gelatinous, 144A in color, about 4 mm in diameter and 2 mm in depth.

Reproductive organs:

*Gynoecium*.—1 Pistil, about 2.5 cm in length, 1.5 mm in width; style is 145B in color and 1.3 cm in length; stigma minute, too small to read color, ovary is superior with a stipe, 144A in color, 7 mm in length and 1.5 mm in width; stipe is 144B in color, 3 mm in length and 1.5 mm in width.

*Androcoecium*.—10 stamens, not united, 1.8 cm in length and 1 mm in width; filament is 1.65 cm in length, 1 mm in width and 145C in color; anther is dorsifixed, 1.5 mm in length and width and 199C in color, pollen is abundant and 14B in color.

*Fruit*.—An inflated pod, technically a legume, average of 1 produced per inflorescence (open-pollinated), elliptic-oblong in shape, average of 3 cm in length by 1.5 cm in width with a beak approx. 1.5 cm in length, color of outer surface and inner surface when mature is a blend of 202A and 202B, walls 1.5 mm and hard at maturity, seed; average of 3 per fruit (open-pollinated), 202A in color, oval with the hilum side more or less straight, seed compressed to flattish, 5 mm in length, 3 mm in width and 2 mm in thickness.

It is claimed:

1. A new and distinct cultivar of *Baptisia* plant named 'Lavender Rose' as herein illustrated and described.

* * * * *